United States Patent [19]

Leonard et al.

[11] 4,026,669

[45] May 31, 1977

[54] VARIABLE CAPACITY RESERVOIR ASSEMBLY

[75] Inventors: Ronald James Leonard, Harvard; Evelyn Miller, Lindenhurst, both of Ill.

[73] Assignee: Baxter Laboratories, Inc., Deerfield, Ill.

[22] Filed: July 14, 1975

[21] Appl. No.: 595,901

[52] U.S. Cl. .................... 23/258.5 R; 23/258.5 A; 128/214 D; 128/DIG.3; 150/1; 229/56

[51] Int. Cl.² .................... A61M 1/03; A61M 5/14

[58] Field of Search .... 23/258.5, 258.5 A, 258.5 B, 23/258.5 BH, 258.5 M, 258.5 MH; 128/214 D, 272, DIG. 3, DIG. 24; 229/56, 65; 150/1, 3

[56] References Cited

UNITED STATES PATENTS

| | | | |
|---|---|---|---|
| 2,663,298 | 12/1953 | Rose | 128/214 |
| 2,848,995 | 8/1958 | Ryan | 128/214 D |
| 2,969,063 | 1/1961 | Broman | 128/214 |
| 3,074,451 | 1/1963 | Whitney | 128/214 D X |
| 3,211,144 | 10/1965 | Nehring | 128/214 D |
| 3,545,671 | 12/1970 | Ross | 128/214 D X |
| 3,729,377 | 4/1973 | Leonard | 23/258.5 BH |
| 3,853,479 | 12/1974 | Talonn et al. | 23/258.5 BH |
| 3,890,969 | 6/1975 | Fischel | 23/258.5 MH |

FOREIGN PATENTS OR APPLICATIONS 1,410,495 10/1975 United Kingdom

OTHER PUBLICATIONS

Clinical Comparison of the General Electric Pierce Membrane Lung & Bubble Oxygenator for Prolonged Cardiopulmonary Bypass, Surgery vol. 74, No. 6, pp. 874-879.

*Primary Examiner*—Morris O. Wolk
*Assistant Examiner*—Michael S. Marcus
*Attorney, Agent, or Firm*—Paul C. Flattery; George H. Gerstman; William K. Wells

[57] ABSTRACT

A variable capacity reservoir assembly for use in a blood oxygenation system which includes a collapsible reservoir and an elongated unitary clamp. The reservoir is of fluid-impermeable flexible material and includes an expandable portion capable of holding a predetermined maximum volume of blood. The reservoir also includes one main blood inlet and one main blood outlet. The clamp is bifurcated and slidably engages the reservoir, preferably between the inlet and the outlet and grasps the expandable portion so as to control the expansion thereof and thereby control its blood holding capacity.

3 Claims, 6 Drawing Figures

U.S. Patent  May 31, 1977  Sheet 1 of 2  4,026,669
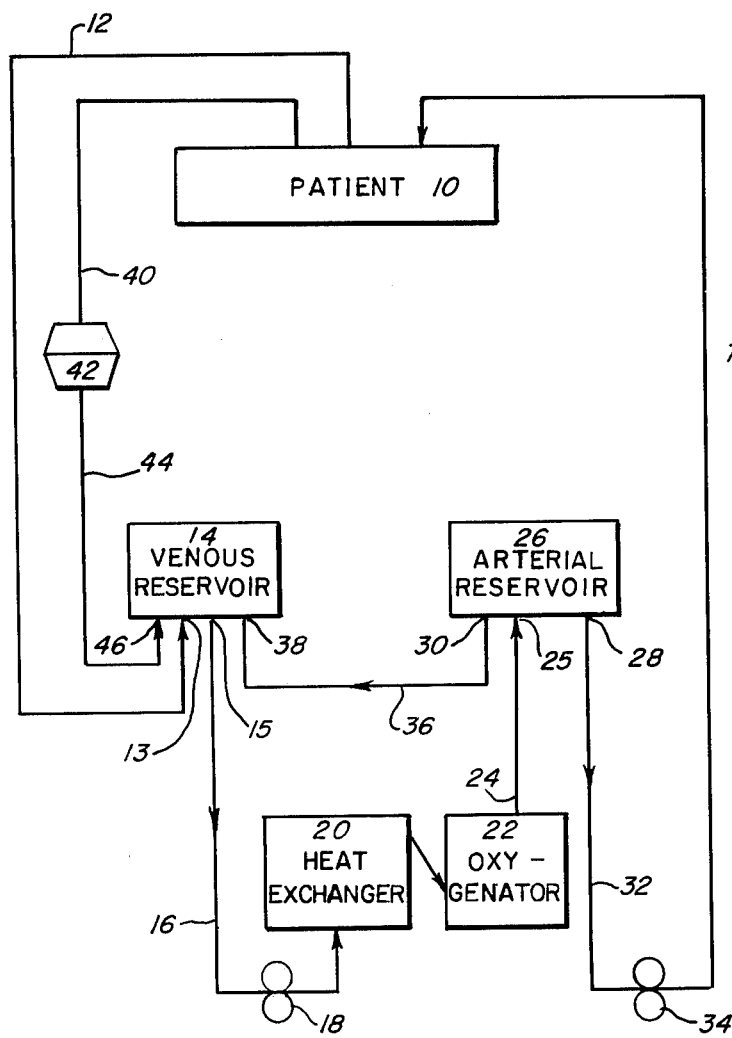
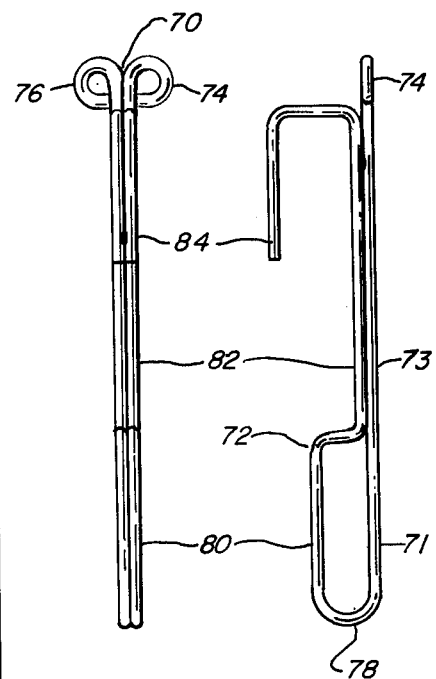
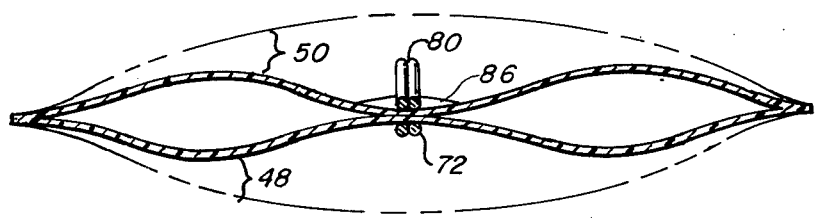

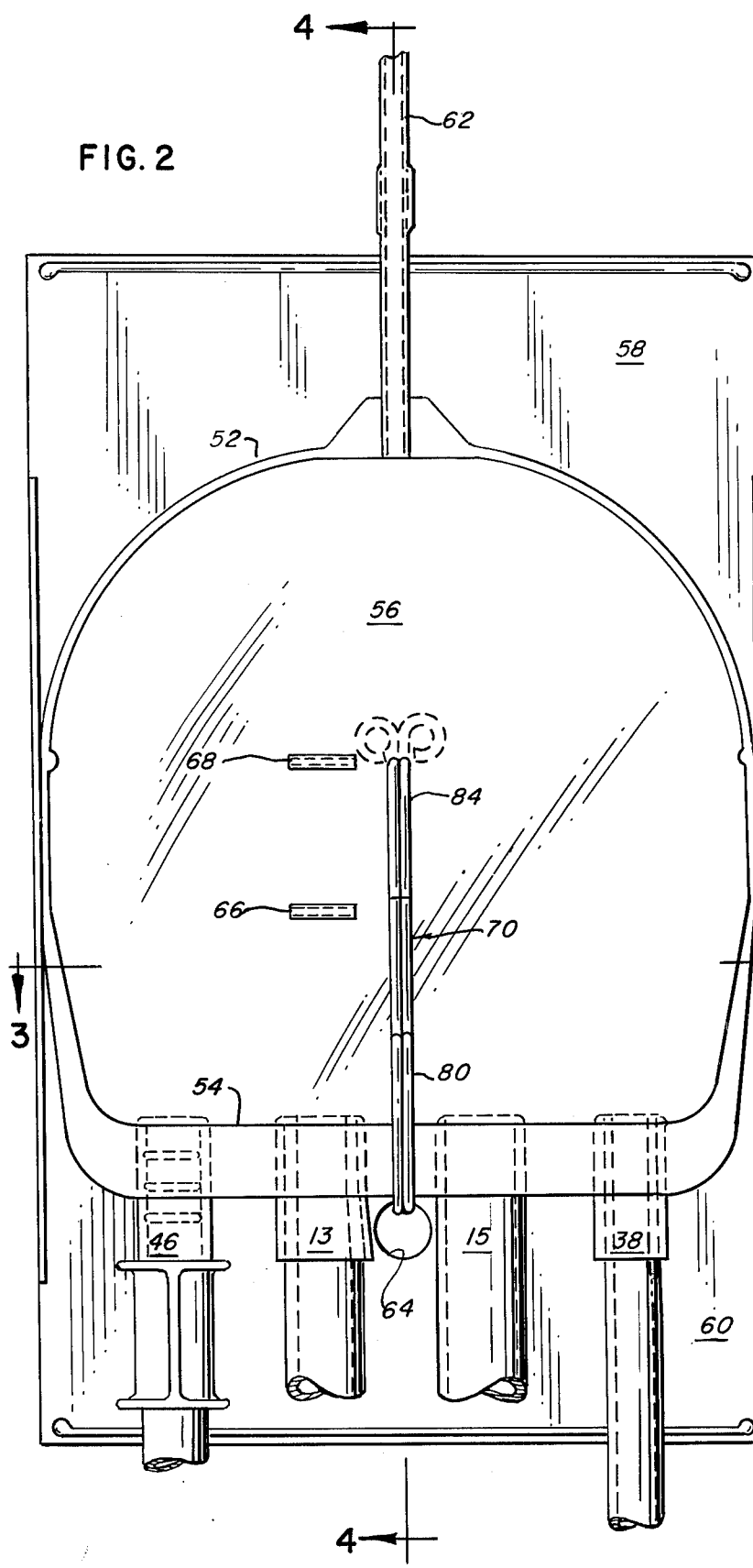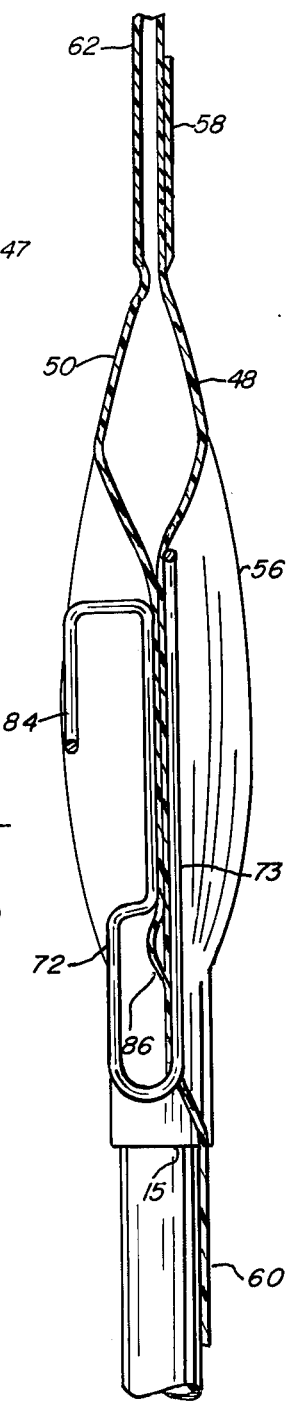

VARIABLE CAPACITY RESERVOIR ASSEMBLY

BACKGROUND OF THE INVENTION

This invention relates to a membrane blood oxygenator system, and more particularly, to a blood reservoir for use therein.

Membrane oxygenator systems typically use flexible and collapsible reservoirs to contain blood volume within the extracorporeal circuit. These reservoirs are multifunctional. They allow the storage of priming solution, contain excess fluid as a result of patient volume changes, and act as bubble traps for gaseous emboli. Collapsible reservoirs have the added feature of collapsing if accidentally pumped dry, so as to prevent the entry of air into the oxygenator system which might cause air embolism in the patient.

Present collapsible reservoirs are of a fixed maximum size. It is generally desirable for best bubble removal and easiest operation to maintain the reservoirs completely full. In opposition to this, it is generally desirable to use a minimum volume of priming solution in the system in order to limit patient blood dilution or to limit the amount of blood needed to prime the system. Excessive blood dilution can adversely affect the patient's hematocrit level while excessive amounts of blood increase the possibility of transmitting hepatitis to the patient. The relative balance between best bubble removal and minimum priming volume varies with patient size, conditions during the operation, and operator technique. Changes in operating conditions include occasional large increases in blood volume due to the surgeon's removal of blood from the incision site. In order to satisfy all conditions, a variety of fixed reservoir sizes would be required. However, this still would not allow for changes occurring during the operation.

It is therefore an object of this invention to provide a universal reservoir which can be used under varying conditions.

The foregoing and other objects of this invention will be apparent from the following description and appended claims.

SUMMARY OF THE INVENTION

There is provided by this invention a reservoir assembly wherein the volume thereof can be controllably varied so as to balance bubble removal against the amount of priming volume and meet the varying conditions of patient size, operating conditions and operator technique. The assembly includes a blood reservoir and means for controllably adjusting the reservoir volume.

In one embodiment, the reservoir is flexible and collapsible, and the volume thereof is controlled by a slidable bifurcated clamp which grasps the reservoir and prevents the reservoir from expanding to its maximum extent, thereby controlling the expansion and thus the volume of the reservoir. The clamp is slidable so as to permit volume control over a predetermined range. Preferably, the clamp is positioned between the reservoir's main blood inlet and main blood outlet so as to enhance the reservoir's bubble trap effect. The clamp also includes a bridge portion that permits the formation of a small passageway in the reservoir for the flow of a small amount of blood between the inlet and outlet when maximum clamping is effected so as to permit pumping when maximum reaction is required.

BRIEF DESCRIPTION OF THE DRAWINGS

FIG. 1 is a schematic flow diagram of an extracorporeal oxygenation circuit for a membrane oxygenator system which includes two variable capacity reservoir assemblies;

FIG. 2 is a front view of a variable capacity reservoir assembly with the clamp shown in the maximum clamping position;

FIG. 3 is a horizontal cross-sectional view taken substantially along line 3—3 of FIG. 2 and also illustrating in broken line the maximum expansion of the reservoir when the clamp is removed;

FIG. 4 is a vertical cross-sectional view taken substantially along line 4—4 of FIG. 2 illustrating the emergency fluid-flow passageway;

FIG. 5 is a front view of the clamp; and

FIG. 6 is a side view of the clamp.

DESCRIPTION OF THE ILLUSTRATIVE EMBODIMENT

The System

Referring now to the drawings, venous blood flows from the patient 10 through the venous inlet line 12 to the venous reservoir inlet 13 and then into the venous reservoir assembly 14. The venous blood exits the reservoir assembly 14 through the venous reservoir outlet 15 and then flows through the venous outlet line 16 to the venous roller pump 18 and into the heat exchanger 20. The heated blood exists the exchanger 20 and flows through the membrane oxygenator 22. (A suitable oxygenator is available from Travenol Laboratories, Inc., under Catalog No. 5M316.) The oxygenated or arterial blood flows from the oxygenator through the arterial reservoir inlet line 24 to the arterial reservoir inlet 25 and into the arterial reservoir assembly 26.

The arterial reservoir assembly 26 is provided with a primary or arterial blood outlet 28 and a recirculating blood outlet 30. Blood flowing from the primary outlet 28 flows through the arterial outlet line 32 to the arterial roller pump 34 and then to the patient 10. In order to assure proper flow, the venous pump is operated approximately ten percent faster than the arterial pump. In order to accommodate the difference in flow, some arterial blood is directed from the arterial reservoir assembly 26 through the recirculating blood outlet 30 through a recirculation line 36 and into the venous reservoir assembly 14 through a recirculating blood inlet 38.

Occasionally the surgeon will remove blood and debris from the surgical site by a suction apparatus (not shown) which directs such blood and debris along a suction line 40 to a cardiotomy reservoir 42 where it is filtered (such cardiotomy reservoirs are available from Travenol Laboratories, Inc., under Catalog No. 5M0305). The filtered blood then flows through line 44 to the venous reservoir assembly 14 and enters the reservoir assembly through a cardiotomy inlet 46.

The Reservoir Assembly

The arterial and venous reservoir assemblies are identical except for the various connections made to the reservoirs as described hereinafter. Each of the assemblies include a reservoir and a volume adjusting clamp.

For example, the venous reservoir assembly 14 includes a reservoir 47, which is formed from two flexible and transparent vinyl sheets 48 and 50 which are placed back-to-back and heat-sealed along the seal lines 52 and 54. The seal lines define: (1) an expandable liquid-tight blood or volume containing portion 56 which receives and holds the blood and (2) the upper and lower flaps 58 and 60. An atmospheric vent 62 at the top of the reservoir extends from the blood containing portion through the seal line 52 and opens to atmosphere. The venous reservoir inlet 13, cardiotomy blood inlet 46, venous reservoir outlet 15, and venous recirculating inlet 38, each extend through the seal line 54 into the blood containing portion 56.

The lower flap 60 includes a clamp-receiving aperture 64 positioned adjacent seal line 54 and between (1) the venous reservoir inlet 13 and (2) the venous reservoir outlet 15. The front sheet 50 is also provided with volume indicating marks or indicia 66 and 68 which are vertically positioned above the clamp aperture.

The venous reservoir assembly also includes a volume controlling clamp or clip 70. The clamp 70 is a bifurcated bent wire member having a straight-back portion 71 and a shaped front portion 72. The back 71 includes a spine 73 that terminates at its top end in a pair of retaining rings 74 and 76. A bight 78 at the lower end of the spine joins the back 71 to the front 72. The front is shaped such that it includes a lower or bridge portion 80 that is spaced from the spine and a longer upper or clamp portion 82 that resiliently engages the spine. The front portion terminates in a hook-like handle 84 which can be manually grasped. The clamp is formed of a single piece of wire and is formed in such a manner that the ends of the wire are bent inwardly to form the rings 74 and 76 to minimize exposure of sharp edges which could puncture the bag.

In order to install the clamp on the reservoir, either the front portion 72 or back portion 71 of the clamp 70 is passed through the flap aperture 64. In a non-clamping position, both the front and back of the clamp are positioned forwardly of the lower flap 60 and the rings 74 and 76, which together are wider than the diameter of the aperture 64, retain the clamp on the lower flap in a storage position.

THE OPERATION

In operation, when the clamp is in the storage position, blood entering the volume containing portion 56 spreads the front and back sheets apart and thereby expands the portion 56 to its maximum volume as shown in broken line in FIG. 3.

When it becomes necessary or desirable to reduce the capacity of the volume containing portion, the clamp handle 84 is grasped and raised so that the clamp's back portion 71 slides against the outer surface of the back sheet 48 and the clamp's front portion 72 slides against the outer surface of the front sheet 50. The clamp squeezes or pinches those portions of the sheets between it together, reducing the maximum separation of the sheets and thereby reducing the blood containing capacity of the blood containing portion, as best shown in FIG. 3. As the clamp is raised, greater reduction in capacity is achieved.

When the reservoir is clamped, the clamped portion acts as a barrier to direct flow and the bulk of the flow is directed from the cardiotomy and venous blood inlets over the clamped portion to the venous outlet on the other side of the clamp.

In the full-clamping position, as shown in FIGS. 2 and 4, the space between the clamp back 71 and the lower or bridge portion 80 of the clamp front 72 permits formation of a small passage 86 for indirect flow of a relatively small amount of blood through the clamped portion or barrier. This indirect flow allows blood to be pumped out of the reservoir when maximum reaction times are required.

It has been found that the clamping action enhances the bubble removal aspects of the reservoir. Gaseous emboli or bubbles in blood entering the reservoir through the venous inlet 13 or the cardiotomy inlet 46 tend to rise to the top of the reservoir. The bulk of the blood flow passes upwardly over the clamp on the inlet side and downwardly on the outlet side of the clamp. This downward flow is counter to the buoyant tendency of the emboli and enhances the bubbletrap effect. Bubbles leaving the blood, exit the reservoir through the vent 62.

It will be appreciated that suitable changes in the volume can be effected by raising and lowering the clamp. The unclamped reservoir volume is 295 ml. If the clamp is raised to the first clamping position where the top of the clamp is aligned with the first mark 66, the volume is reduced to 230 ml. At the second and maximum position where the top of the clamp is aligned with the second mark 68, the volume is reduced to 180 ml.

In the system, the venous reservoir 47 is clamped as shown and the arterial reservoir is clamped between the arterial blood inlet 25 and the primary arterial blood outlet 28. Such clamping of either type of reservoir separates the main blood inlets and the main blood outlets and enhances the bubble-trap effect.

The recirculation line 36 completes a recirculation circuit between the reservoir assemblies 14 and 26 whereby oxygenated or arterial blood is directed to the venous reservoir. As seen in FIG. 2, the oxygenated blood is prevented by the clamped portion from directly mixing with the bulk of the venous blood entering the venous reservoir through venous and cardiotomy inlets 13 and 46. Thus, the oxygenated blood mixes, in the main, only with venous blood which has passed over the clamped portion.

Although the arterial reservoir is shown with only three lines connected thereto, it is to be understood that for interchangeability and economy of manufacture there is a fourth inlet, as is shown in the venous reservoir, but that the fourth inlet is plugged and not being used in this particular oxygenator system. Otherwise, the arterial and venous reservoirs are identical.

It will be appreciated that numerous changes and modifications can be made to the embodiment shown herein without departing from the spirit and scope of this invention.

What is claimed is:

1. A variable capacity blood reservoir assembly for use in blood oxygenator system, which comprises:
    a blood reservoir including a pair of sheet segments in superposed relation, secured together so as to define a blood receiving volume between said sheet segments which define said blood receiving volume being separable in response to blood entering said volume so that said volume is expandable;
    a blood inlet on one side of said blood reservoir communicating with said blood receiving volume for directing blood flow into said volume;

a blood outlet on said one side of said blood reservoir communicating with said blood receiving volume for directing blood flow from said volume;

a vent located on the side of the blood reservoir opposite to said one side, said vent communicating with said volume for venting said blood receiving volume to atmosphere;

a pinch clamp slidably positioned on said one side between said blood inlet and said blood outlet and slidable toward said opposite side, for controlling the separation of the sheets so as to control the expansion of said volume;

said pinch clamp including an elongated slidable bifurcated clamp constructed to grasp said sheet segments and maintain said sheet segments in back-to-back contact between said bifurcations; and said clamp having an elongated back, and a shaped front which includes an upper clamping portion biased toward said back for holding said sheet segments between said clamp back and said clamp upper portion in said back-to-back contact.

2. A reservoir assembly as in claim 1, wherein said clamp front further includes a lower bridge portion spaced from said back portion so as to permit expansion of said sheet segments between said back and bridge portions.

3. A reservoir assembly as in claim 2, wherein said clamp is formed of shaped wire and said back and said upper portions are resiliently biased toward each other, and said clamp further includes handle means on one side thereof for moving said clamp.

* * * * *

UNITED STATES PATENT AND TRADEMARK OFFICE
CERTIFICATE OF CORRECTION

PATENT NO. : 4,026,669
DATED : May 31, 1977
INVENTOR(S) :

It is certified that error appears in the above-identified patent and that said Letters Patent are hereby corrected as shown below:

Column 2, line 34, delete "5M316" and substitute therefor --5M0316--.

Signed and Sealed this

Thirty-first Day of January 1978

[SEAL]

Attest:

RUTH C. MASON
Attesting Officer

LUTRELLE F. PARKER
Acting Commissioner of Patents and Trademark